(12) United States Patent
Vaillancourt (10) Patent No.: US 10,278,676 B2
(45) Date of Patent: May 7, 2019

(54) SAFETY SHIELD FOR A NEEDLE ASSEMBLY

(76) Inventor: Michael J. Vaillancourt, Chester, NJ (US)

( * ) Notice: Subject to any disclaimer, the term of this patent is extended or adjusted under 35 U.S.C. 154(b) by 1402 days.

(21) Appl. No.: 13/535,060

(22) Filed: Jun. 27, 2012

(65) Prior Publication Data

US 2014/0005571 A1  Jan. 2, 2014

(51) Int. Cl.
*A61M 5/32* (2006.01)
*A61B 10/02* (2006.01)
*A61B 17/34* (2006.01)
*A61B 90/00* (2016.01)

(52) U.S. Cl.
CPC ...... *A61B 10/0233* (2013.01); *A61B 17/3494* (2013.01); *A61M 5/3213* (2013.01); *A61B 2017/3405* (2013.01); *A61B 2090/0801* (2016.02)

(58) Field of Classification Search
CPC .......... A61B 5/15003; A61B 5/150389; A61B 5/153; A61B 5/15074; A61B 5/14; A61B 5/1405; A61B 5/150503; A61B 5/150633; A61B 5/1444; A61B 17/3496
USPC ................. 600/562, 564, 566, 567; 604/171
See application file for complete search history.

(56) References Cited

U.S. PATENT DOCUMENTS

| | | | | |
|---|---|---|---|---|
| 3,613,684 A | * | 10/1971 | Sheridan | 604/264 |
| 3,817,250 A | * | 6/1974 | Weiss et al. | 128/207.29 |
| 4,022,191 A | * | 5/1977 | Jamshidi | A61B 10/0283 600/566 |
| 4,535,773 A | * | 8/1985 | Yoon | 606/185 |
| 4,559,042 A | * | 12/1985 | Votel | A61M 5/3213 604/192 |
| 4,573,975 A | * | 3/1986 | Frist | A61M 5/3213 604/192 |
| 4,639,249 A | * | 1/1987 | Larson | 604/198 |
| 4,733,662 A | * | 3/1988 | DeSatnick et al. | 606/171 |
| 4,767,412 A | * | 8/1988 | Hymanson | A61M 5/3213 294/131 |
| 4,781,697 A | * | 11/1988 | Slaughter | A61M 5/3213 604/192 |
| 4,799,927 A | * | 1/1989 | Davis | A61M 5/3213 604/192 |
| 4,850,961 A | * | 7/1989 | Wanderer et al. | 604/508 |
| 4,892,525 A | * | 1/1990 | Hermann, Jr. | A61M 5/3213 206/365 |
| 4,900,309 A | * | 2/1990 | Netherton | A61M 5/3213 336/192 |
| 4,906,236 A | * | 3/1990 | Alberts et al. | 604/198 |
| 4,917,672 A | * | 4/1990 | Terndrup et al. | 604/192 |
| 5,018,530 A | * | 5/1991 | Rank | A61B 17/3403 600/435 |
| 5,078,694 A | * | 1/1992 | Wallace | A61M 39/04 604/192 |
| 5,117,978 A | * | 6/1992 | Blumenfeld | A61B 5/0492 206/364 |

(Continued)

*Primary Examiner* — May A Abouelela
(74) *Attorney, Agent, or Firm* — Francis C. Hand; Bryne Carella (57) ABSTRACT

The safety shield is comprised a one piece body, e.g. of biocompatible plastic, having a hollow stem 11 and a disc-shaped collar 13 extending radially outwardly from one end of the hollow stem 11. The safety shield is mounted by the user in friction fit manner in a hub of an implanted needle and serves as a guide for the insertion of a biopsy needle into the implanted needle.

3 Claims, 7 Drawing Sheets

(56) References Cited

U.S. PATENT DOCUMENTS

| | | | |
|---|---|---|---|
| 5,125,413 A * | 6/1992 | Baran | 600/567 |
| 5,147,308 A * | 9/1992 | Singer | 604/117 |
| 5,152,779 A * | 10/1992 | Sanagi | 606/205 |
| 5,195,533 A * | 3/1993 | Chin et al. | 600/567 |
| 5,217,441 A * | 6/1993 | Shichman | 604/536 |
| 5,295,974 A * | 3/1994 | O'Laughlin | 604/198 |
| 5,304,148 A * | 4/1994 | Lannoye | A61M 5/3213 128/919 |
| 5,312,416 A * | 5/1994 | Spaeth et al. | 606/114 |
| 5,342,315 A * | 8/1994 | Rowe | A61B 17/3462 604/167.06 |
| 5,364,372 A * | 11/1994 | Danks et al. | 604/264 |
| 5,400,798 A * | 3/1995 | Baran | 600/567 |
| 5,738,220 A * | 4/1998 | Geszler | A61N 1/056 206/365 |
| 5,746,727 A * | 5/1998 | Graves | A61M 25/0631 604/198 |
| 5,817,034 A * | 10/1998 | Milliman et al. | 600/566 |
| 6,007,519 A * | 12/1999 | Rosselli | 604/164.01 |
| 6,096,005 A * | 8/2000 | Botich et al. | 604/110 |
| 6,099,505 A * | 8/2000 | Ryan et al. | 604/167.04 |
| 6,213,957 B1 * | 4/2001 | Milliman et al. | 600/566 |
| 6,336,915 B1 * | 1/2002 | Scarfone et al. | 604/171 |
| 6,613,063 B1 * | 9/2003 | Hunsberger | 606/185 |
| 6,702,760 B2 * | 3/2004 | Krause et al. | 600/564 |
| 6,863,662 B2 * | 3/2005 | Luther | 604/264 |
| 6,955,653 B2 * | 10/2005 | Eggers | 600/564 |
| 7,001,396 B2 * | 2/2006 | Glazier et al. | 606/108 |
| 7,063,703 B2 * | 6/2006 | Reo | 606/79 |
| 7,153,319 B1 * | 12/2006 | Haberland et al. | 606/185 |
| 7,494,473 B2 * | 2/2009 | Eggers et al. | 600/582 |
| 7,738,968 B2 * | 6/2010 | Bleich | 607/117 |
| 7,985,216 B2 * | 7/2011 | Daily et al. | 604/533 |
| 8,002,713 B2 * | 8/2011 | Heske et al. | 600/566 |
| 8,012,102 B2 * | 9/2011 | McCullough et al. | 600/566 |
| 8,043,229 B2 * | 10/2011 | Mulvihill et al. | 600/568 |
| 8,096,957 B2 * | 1/2012 | Conquergood et al. | 600/567 |
| 8,128,577 B2 * | 3/2012 | Viola | 600/568 |
| 8,170,648 B2 * | 5/2012 | Field et al. | 600/431 |
| 2003/0114797 A1 * | 6/2003 | Vaillancourt et al. | 604/171 |
| 2005/0165328 A1 * | 7/2005 | Heske et al. | 600/566 |
| 2006/0206132 A1 * | 9/2006 | Conquergood et al. | 606/180 |
| 2007/0149893 A1 * | 6/2007 | Heske et al. | 600/566 |
| 2008/0097239 A1 * | 4/2008 | Chang et al. | 600/562 |
| 2009/0005743 A1 * | 1/2009 | Vaillancourt et al. | 604/263 |
| 2009/0247900 A1 * | 10/2009 | Zimmer | 600/564 |
| 2009/0264794 A1 * | 10/2009 | Kodama | 600/567 |
| 2010/0217151 A1 * | 8/2010 | Gostout et al. | 600/565 |
| 2011/0034828 A1 * | 2/2011 | Holmin et al. | 600/567 |
| 2012/0065590 A1 * | 3/2012 | Bierman et al. | 604/164.05 |
| 2012/0289858 A1 * | 11/2012 | Ouyang et al. | 600/562 |

* cited by examiner

SAFETY SHIELD FOR A NEEDLE ASSEMBLY

This invention relates to a safety shield for a needle assembly. More particularly, this invention relates to a safety shield for a biopsy needle assembly.

As is known, various types of biopsy needle assemblies have been known for the extraction of tissue samples from a patient for various reasons. Generally, the biopsy needle assemblies include a biopsy needle that passes through a sheath extending from a main housing such as described in U.S. Pat. No. 6,699205. Also known are biopsy needles, such as described in U.S. Pat. No. 4,022,191, wherein a biopsy needle extending from a specimen collecting system is covered by a sheath prior to use.

One procedure for using a biopsy needle assembly is to employ a needle assembly having a hollow needle and a stylet that passes through the hollow needle to make an initial insertion into the tissue of a patient from which a sample is to be taken. Once the needle assembly is inserted, the stylet is removed and a biopsy needle of the biopsy needle assembly is inserted manually into the implanted hollow needle to obtain a tissue sample. Usually, a user holds the implanted hollow needle in position with one hand while manipulating the biopsy needle assembly with a second hand in order to guide the biopsy needle into and through the hollow needle. Where the biopsy needle extends from a hub of the biopsy needle assembly in an exposed manner while being of a relatively long length, a risk of a "stick" arises in aligning the sharp tip of the biopsy needle with the implanted hollow needle.

Accordingly, it is an object of the invention to reduce the risk of a stick during a biopsy procedure when inserting a biopsy needle into an implanted hollow needle.

It is another object of the invention to provide a low cost safety shield for a biopsy needle assembly.

It is another object of the invention to provide a safety shield for a biopsy needle assembly that is simple to use.

Briefly, the invention provides a safety shield for use on a needle assembly implanted in a patient for the guidance of a biopsy needle of a biopsy needle assembly into the needle assembly.

The safety shield is made as a one piece body, for example of plastic, with a hollow stem disposed on a longitudinal axis and having a passage extending therethrough and a disc-shaped collar extending radially outwardly from one end of the hollow stem and circumferentially about the passage.

The needle assembly includes a hub having a longitudinal passage and a hollow needle that extends longitudinally from the hub in communication with the passage. In addition, as is usual, the needle assembly also includes a trocar stylet having a hub and a stylet extending from hub through the hollow needle. In use, the needle assembly is manipulated to pass into the tissue of a patient to be sampled while employing. the stylet to pierce the skin of the patient and enter into the target tissue. Once in place, the trocar stylet is removed leaving the hollow needle implanted in the tissue.

The stem of the safety shield is sized to fit into the passage in the hub. Hence, once the trocar stylet is removed from the hollow needle, the stem of the safety shield is inserted into the passage of the hub with the collar of the safety shield extending outwardly of the hub.

In one embodiment, the stem of the safety shield is made of a slightly conical shape to fit into the passage of the hub with a friction fit. The shape of the stem may also be a luer taper which would match the majority of hubs to be inserted therein.

In another embodiment, the stem of the safety shield has a plurality of longitudinal slits extending from a distal end towards the collar to permit constriction of the stem when passing into the hub of the needle assembly thereby creating a tighter friction fit within the hub.

The collar of the safety shield is of a circular or an oval shape with a conical proximal surface for guiding the tip of a biopsy needle into the hub of the needle assembly.

In another embodiment, an integral guide block is integrally formed on the concave surface of the collar of the safety shield for directing a biopsy needle towards the passage defined by the needle of the implanted needle assembly. To this end, the guide block may also have a longitudinally extending recess coaxial with hollow stem.

In another embodiment, the safety shield has a pair of mounting blocks extending distally from the collar and transversely spaced from opposite sides of the stem for engaging opposite sides of the hub of the needle assembly in a snap fit manner.

The biopsy needle assembly is of conventional structure including a longitudinally extending biopsy needle to be disposed concentrically in an implanted hollow needle of the needle assembly after passing through the hollow stem of the safety shield.

In order to use the safety shield, the needle assembly with the trocar stylet therein is employed in a conventional manner to access the tissue of a patient to be sampled. After removal of the trocar stylet and while holding the hub of the implanted needle with one hand, the user would insert the stem of the safety shield firmly into the passage in the hub. Next, with a second hand, the user would manipulate the biopsy needle assembly to insert the tip of the biopsy needle into the hollow stem of the safety shield and then to insert the biopsy needle into and through the implanted hollow needle.

During manipulation of the biopsy needle into the hollow stem of the safety shield, the outwardly extending collar serves as a shield between the fingers of the user holding the hub of the implanted needle assembly and the tip of the biopsy needle. In addition, the collar serves as a guide for guiding the tip of the biopsy needle into the hollow stem of the safety shield.

These and other objects and advantages of the invention will become more apparent from the following detailed description taken in conjunction with the accompanying drawings wherein:

Figure 1:
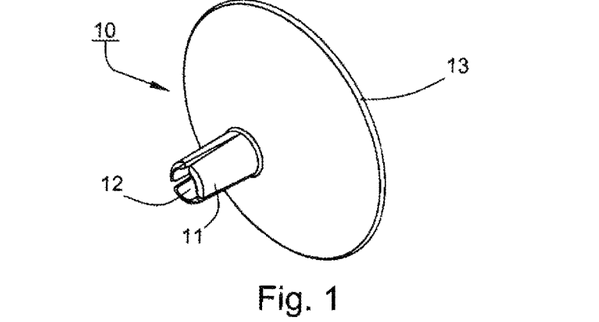
FIG. 1 illustrates a perspective view of a safety shield constructed in accordance with the invention.

Referring to FIG. 1, the safety shield 10 is comprised a one piece body, e.g. of biocompatible plastic, having a hollow stem 11 disposed on a longitudinal axis and having a passage 12 extending therethrough and a disc-shaped collar 13 extending radially outwardly from and longitudinally away from one end of the hollow stem 11 and circumferentially about the passage 12.

Figure 7:
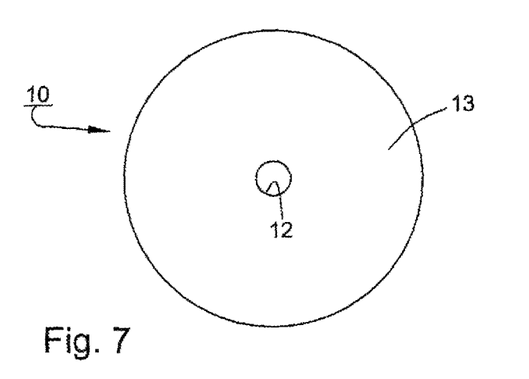
FIG. 7 illustrates a top view of the safety shield of FIG. 1.
Figure 8:
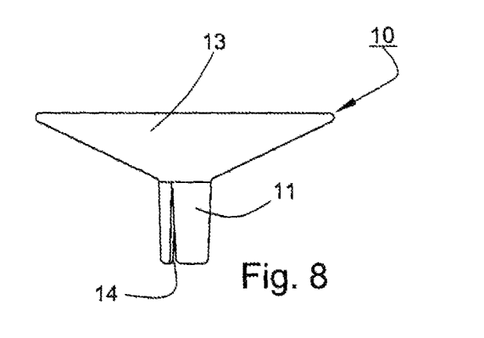
FIG. 8 illustrates a side view of the safety shield of FIG. 1.
Figure 9:
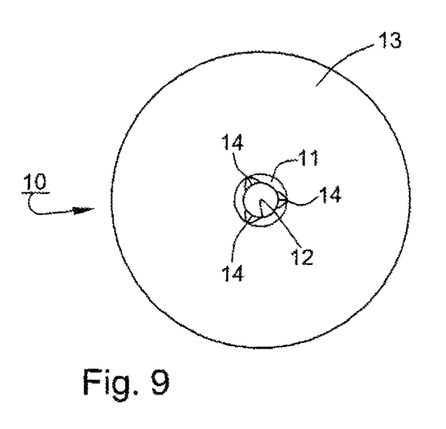
FIG. 9 illustrates a bottom view of the safety shield of FIG. 1.
Figure 10:
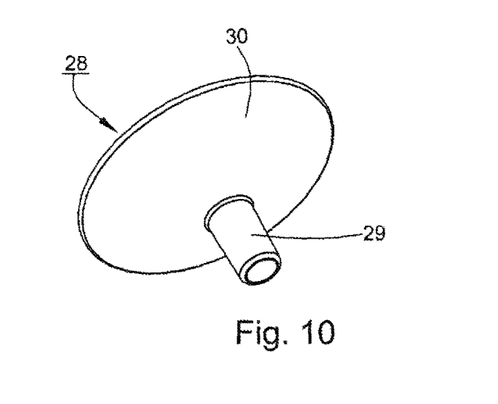
FIG. 10 illustrates a perspective view of a modified safety shield constructed in accordance with the invention.
Figure 11:
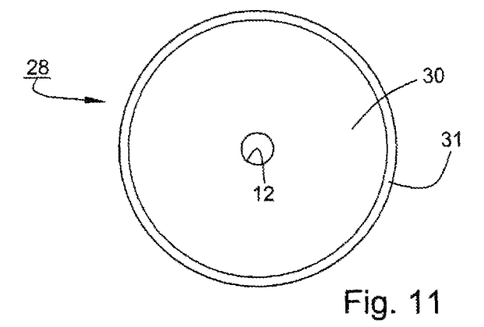
FIG. 11 illustrates a top view of the safety shield of FIG. 10.
Figure 12:
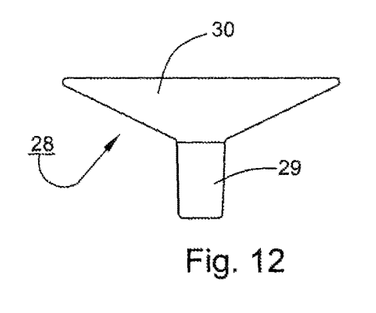
FIG. 12 illustrates a side view of the safety shield of FIG. 10.
Figure 13:
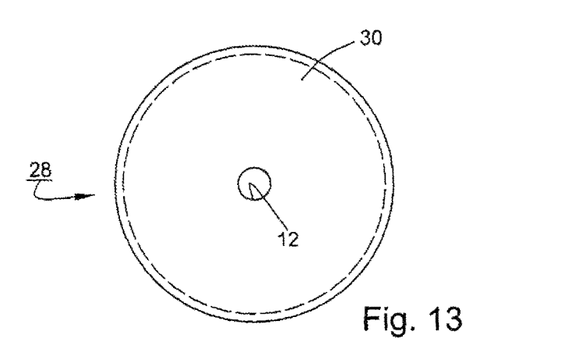
FIG. 13 illustrates a bottom view of the safety shield of FIG. 10.
Figure 14:
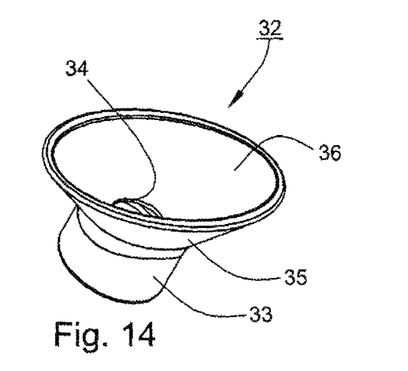
FIG. 14 illustrates a perspective view of a safety shield of ovate shape constructed in accordance with the invention.
Figure 15:
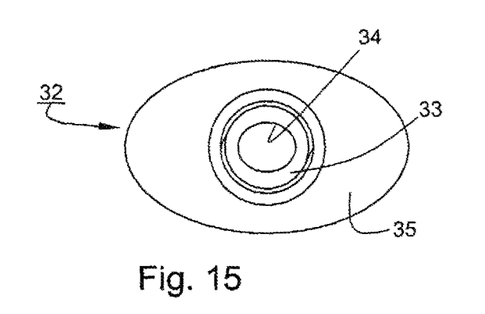
FIG. 15 illustrates a bottom view of the safety shield of FIG. 14.
Figure 16:
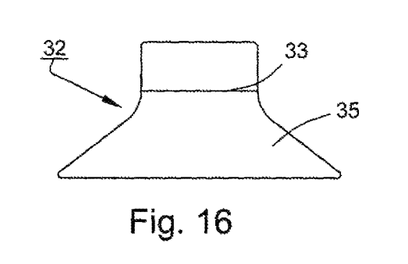
FIG. 16 illustrates a side view of the safety shield of FIG. 14.
Figure 17:
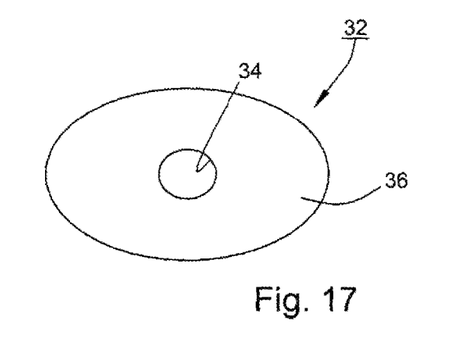
FIG. 17 illustrates a top view of the safety shield of FIG. 14.
Figure 18:
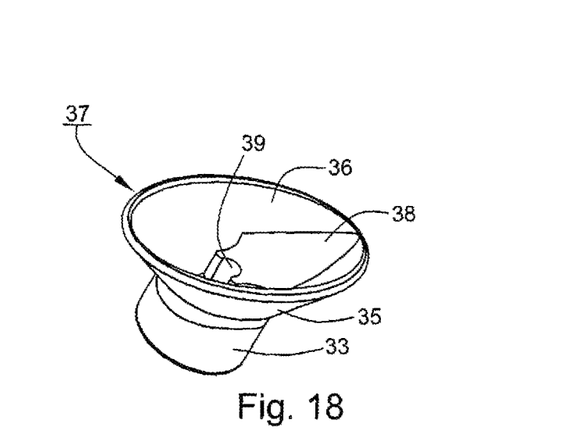
FIG. 18 illustrates a perspective view of a safety shield with a guide block in accordance with the invention.
Figure 19:
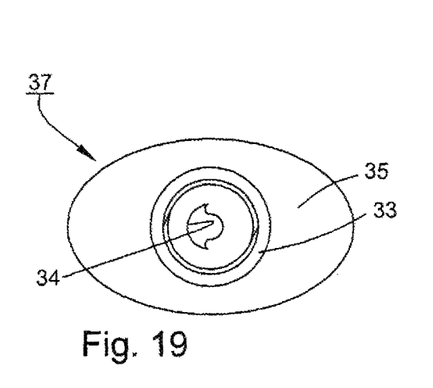
FIG. 19 illustrates a bottom view of the safety shield of FIG. 18.
Figure 20:
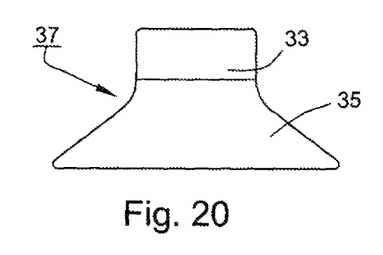
FIG. 20 illustrates a side view of the safety shield of FIG. 18.
Figure 21:
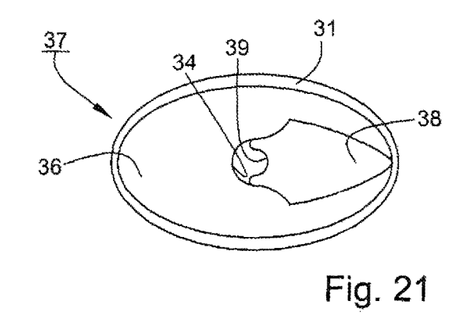
FIG. 21 illustrates a top view of the safety shield of FIG. 18.
Figure 22:
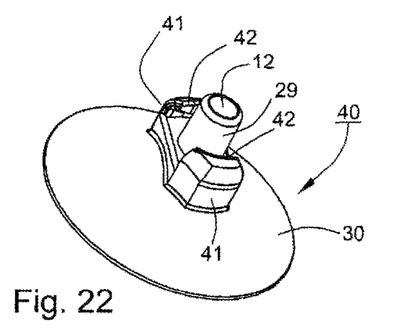
FIG. 22 illustrates a perspective view of a safety shield with a pair of mounting blocks in accordance with the invention.
Figure 23:
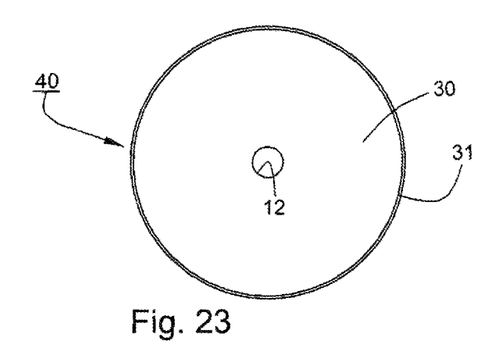
FIG. 23 illustrates a top view of the safety shield of FIG. 22.
Figures 24, 25:
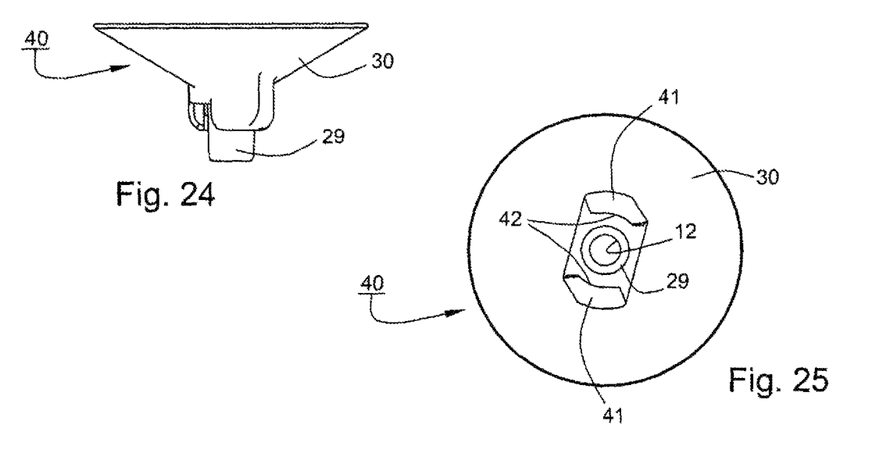
FIG. 24 illustrates a side view of the safety shield of FIG. 22.
FIG. 25 illustrates a bottom view of the safety shield of FIG. 22.

Referring to FIGS. 7, 8 and 9, wherein like reference characters indicate like parts as above, the stem 11 of the safety shield 10 is of circular shape and is provided with a plurality of longitudinal slits 14 that extend from a distal end towards the collar 13. Each slit 14 is of an elongated V-shape with the widest dimension at the distal end of the stem 11. The collar 13 of the safety shield 10 is also of circular shape with a conical proximal surface 15 that extends from the outer periphery of the collar 13 to the outer periphery of the stem 11.

Figure 2:
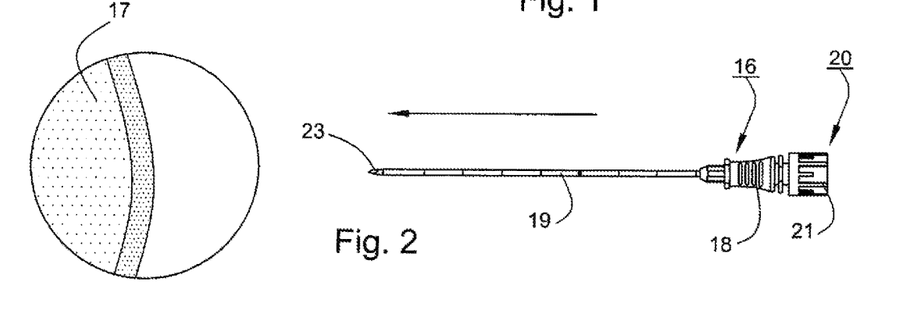
FIG. 2 illustrates the relative positions of a needle assembly and the tissue of a patient to be sampled during a biopsy procedure.

Referring to FIG. 2, during a biopsy procedure, a needle assembly 16 is initially inserted into the tissue 17 of a patient (not shown) to be sampled. As shown, the needle assembly 16 is of conventional construction having a hub 18 with a longitudinal passage therein (not shown) and a hollow needle 19 extending longitudinally from the hub 18 in communication with the passage. In addition, the needle assembly 16 has a trocar stylet 20 including a hub 21 and a stylet 22 (see FIG. 3) extending from the hub 21 through the hollow needle 19. As illustrated, the stylet 22 has a tip 23 that extends outwardly from the hollow needle 19.

Figure 3:
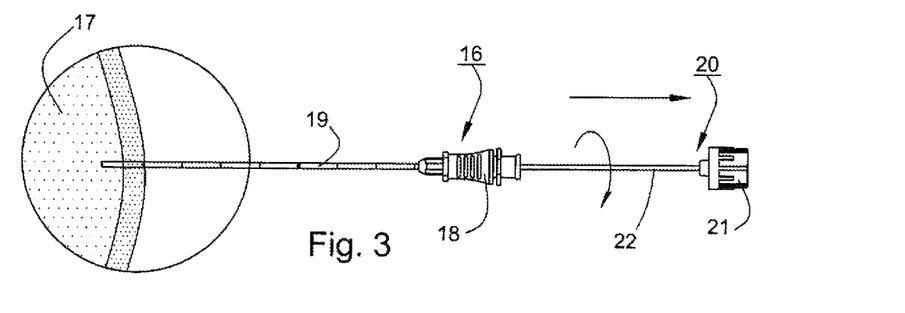
FIG. 3 illustrates the relative positions of the needle assembly and tissue of FIG. 2 during removal of a trocar stylet from the needle assembly during a biopsy procedure.

Referring to FIG. 3, after the needle assembly 16 has been inserted into tissue 17, the trocar stylet 20 is removed from the hollow needle 19 while the hollow needle 19 remains in the tissue 17. Typically, during removal of the trocar stylet 20 from the hollow needle 19 of the needle assembly 16, a user grasps the hub 18 with two fingers of one hand (not shown) while pulling the trocar stylet 20 with the other hand.

Figure 4:
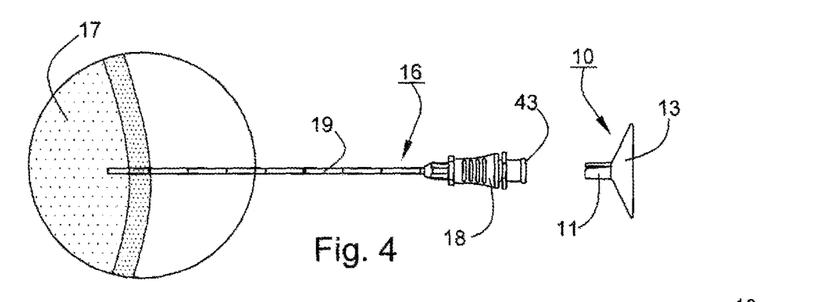
FIG. 4 illustrates the relative positions of the needle assembly of FIGS. 2 and 3 during insertion of a safety shield in accordance with the invention.
Figure 5:
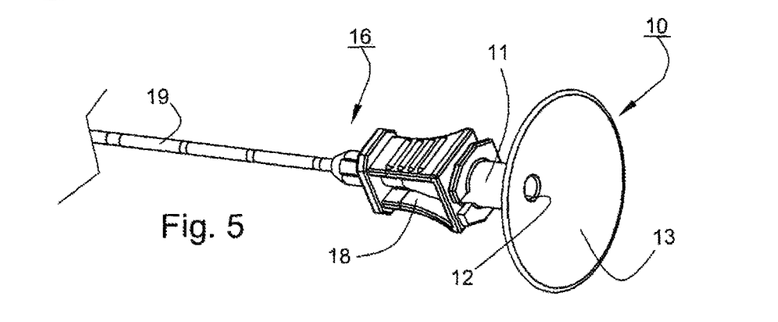
FIG. 5 illustrates a perspective view of a safety shield in accordance with the invention mounted on the hub of a needle assembly.

Referring to FIGS. 4 and 5, after removal of the trocar stylet 20, the user while holding the hub 18 of the tissue implanted needle assembly 16, mounts the safety shield 10 on the hub 18 by inserting the stem 11 into the passage of the hub 18. During this time, the stem 11 constricts by closing of the slits 14 as the passage in the hub 18 is of a slightly conical shape thereby obtaining a tight friction fit of the stem 11 within the passage.

Referring to FIG. 5, once in place, the collar 13 of the safety shield extends radially outwardly of the hub 18 of the needle assembly 16.

Figure 6:
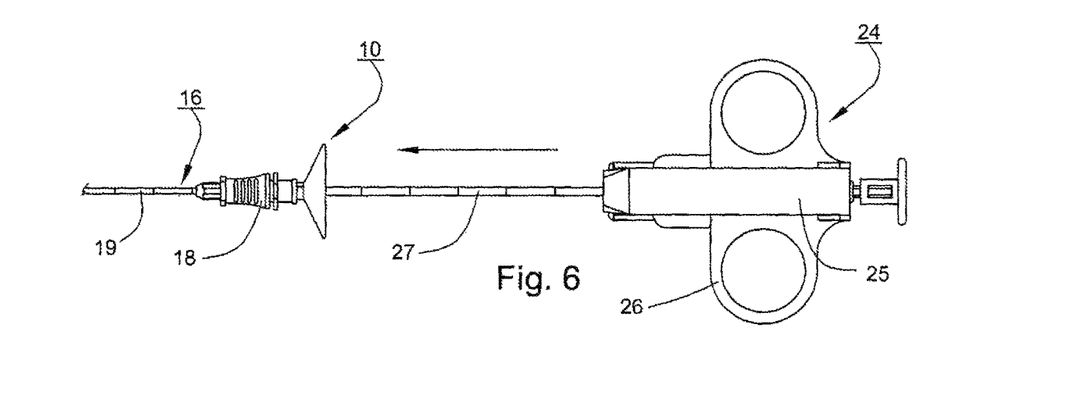
FIG. 6 illustrates the relative positions of a biopsy needle assembly and the safety shield during insertion of the biopsy needle during a biopsy procedure.

Referring to FIG. 6, in order to obtain a sample of the tissue 17, use is made of a biopsy needle assembly 24 of conventional structure having a handle 25 with two finger sized aperture ears 26 for manual manipulation and a biopsy needle 27 that extends longitudinally from the handle 25. Additional components of the biopsy needle assembly are conventional and need not be described in detail.

The biopsy needle 27 is of a length to be disposed concentrically in and to pass through the implanted hollow needle 19 of the needle assembly 16 in order to obtain a sample of the tissue 17.

In order to insert the biopsy needle 27 into the implanted hollow needle 19, the user holds the hub 18 of the implanted hollow needle 19 with two fingers of one hand (not shown) while manipulating the biopsy needle assembly 24 to align the biopsy needle 27 with the passage 12 in the stem 11 of the safety shield 10. Then, the user inserts the tip of the biopsy needle 27 into and through the stem 11 of the safety shield 10 and, thus, into the implanted hollow needle 19 to perform a biopsy procedure.

Referring to FIGS. 10 to 13, wherein like reference characters indicate like parts as above, the safety shield 28 may be made with a stem 29 that has an uninterrupted periphery (i.e. without slits) and a slight conical shape for fitting into the passage of the hub 18 of a needle assembly 16. In addition, the collar 30 may be made with a small flat lip 31 (see FIG. 11) about the outer periphery.

Referring to FIGS. 14 to 17, wherein like reference characters indicate like parts as above, the safety shield 32 may be made with a stem 33 of an enlarged outside diameter for fitting into or about a hub of a needle assembly (not shown) as well as with an enlarged passage 34 of oval cross-sectional shape. In addition, the safety shield 32 may have a collar 35 of oval or ovate shape and a proximal surface 36 of a corresponding conical shape.

Referring to FIGS. 18 to 21, wherein like reference characters indicate like parts as above, the safety shield 37 may be made with an integral guide block 38 on the conical surface 36 for directing a biopsy needle towards the passage 34. As illustrated, the guide block 38 has a longitudinally extending recess 39 coaxial with the passage 34 (see FIG. 21) for guiding a biopsy needle into the passage 34.

The collar 35 may also be provided with a small flat lip 31 (see FIG. 21) about the outer periphery as in the embodiment of FIGS. 10 to 13.

Referring to FIGS. 22 to 25, wherein like reference characters indicate like parts as above, the safety shield 40 may be made with a pair of guide blocks 41 that extend distally from the collar 30 and transversely spaced from opposite sides of the stem 29. Each guide block 41 has an inwardly projecting detent 42 for engaging under a peripheral lip 43 (see FIG. 4) on the hub 18 of a needle assembly 16.

In each of the embodiments of the safety shield, the collar projects outwardly of an implanted needle to protect the fingers of a user against inadvertent sticks from a biopsy needle being inserted into the implanted needle. In addition, the safety shield is made of a shape to facilitate entry of a biopsy needle into the implanted needle.

The invention thus provides an assemblage comprised of a needle assembly with a trocar stylet, a safety shield and a biopsy needle assembly all of which may be packaged in one sterile unit, particularly, for a one-time disposable use.

The invention thus provides a low cost safety shield that reduces the risk of a stick during a biopsy procedure when inserting a biopsy needle into an implanted hollow needle while being simple to use.

What is claimed is:

1. A safety shield comprising a one piece body having a hollow stem disposed on a longitudinal axis and having a passage extending therethrough and a disc-shaped collar extending radially outwardly from one end of said hollow stem and circumferentially about said passage, said hollow stem having at least three longitudinal slits extending from a distal end towards said collar.

2. A safety shield as set forth in claim 1 wherein collar has a conical proximal surface.

3. In combination,
   a needle assembly including a hub having a longitudinal passage therein and a hollow needle extending longitudinally from said hub in communication with said passage; and
   a safety shield having a hollow stem of circular shape disposed in said passage of said hub and a disc-shaped collar extending radially outwardly from one end of said hollow stem and extending radially outwardly of said hub of said needle assembly.

\* \* \* \* \*